US011779268B2

(12) United States Patent
Liu et al.

(10) Patent No.: US 11,779,268 B2
(45) Date of Patent: *Oct. 10, 2023

(54) ELECTRONIC MANAGEMENT OF SLEEP RELATED DATA

(71) Applicant: RESMED INC., San Diego, CA (US)

(72) Inventors: Nathan Zersee Liu, Sydney (AU); Pui Hei Lui, Sydney (AU); Claudio Luca Natoli, Sydney (AU)

(73) Assignee: ResMed Inc., San Diego, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 17/123,791

(22) Filed: Dec. 16, 2020

(65) Prior Publication Data

US 2021/0204869 A1 Jul. 8, 2021

Related U.S. Application Data

(63) Continuation of application No. 15/031,923, filed as application No. PCT/AU2014/050305 on Oct. 24, 2014, now Pat. No. 10,893,831.

(30) Foreign Application Priority Data

Oct. 25, 2013 (AU) .............................. 2013904136

(51) Int. Cl.
*A61B 5/00* (2006.01)
*G16H 50/30* (2018.01)
(Continued)

(52) U.S. Cl.
CPC .......... *A61B 5/4818* (2013.01); *A61B 5/0002* (2013.01); *A61B 5/08* (2013.01);
(Continued)

(58) Field of Classification Search
CPC ....... A61B 5/4818; A61B 5/0002; A61B 5/08; A61B 5/6831; A61B 5/7425; A61B 5/087;
(Continued)

(56) References Cited

U.S. PATENT DOCUMENTS 8,260,006 B1 * 9/2012 Callari ................ G06V 10/751
345/631
8,560,600 B2 10/2013 Otero et al.
(Continued)

FOREIGN PATENT DOCUMENTS

EP 1380937 A1 1/2004
EP 1450277 A2 8/2004
(Continued)

OTHER PUBLICATIONS

Extended European Search Report for Application No. 14855534.5 dated May 24, 2017.
(Continued)

*Primary Examiner* — Maroun P Kanaan
(74) *Attorney, Agent, or Firm* — Botos Churchill IP Law LLP

(57) ABSTRACT

A system and method electronically manages sleep related data obtained by a diagnostic device. The system and method may include collecting sleep data from a patient using a diagnostic device. The sleep data may be stored in a sleep data file and delineated as multiple sleep sessions. A user may access the stored sleep data by selecting a particular sleep session. The sleep data for the selected sleep session may then be extracted from the sleep data file and presented to the user as a combination of image tiles, JavaScript elements, and an event indicator.

24 Claims, 9 Drawing Sheets

(51) Int. Cl.
  *G16H 15/00* (2018.01)
  *A61B 5/08* (2006.01)
  *G16H 30/20* (2018.01)
  *G06T 11/20* (2006.01)
  *G16H 40/63* (2018.01)
  *A61B 5/113* (2006.01)
  *A61B 5/087* (2006.01)
  *A61B 5/1455* (2006.01)

(52) U.S. Cl.
  CPC .......... *A61B 5/6831* (2013.01); *A61B 5/7425* (2013.01); *G06T 11/206* (2013.01); *G16H 15/00* (2018.01); *G16H 30/20* (2018.01); *G16H 50/30* (2018.01); *A61B 5/087* (2013.01); *A61B 5/1135* (2013.01); *A61B 5/14551* (2013.01); *A61B 5/742* (2013.01); *A61B 2560/0475* (2013.01); *G06T 2210/41* (2013.01); *G16H 40/63* (2018.01)

(58) Field of Classification Search
  CPC ... A61B 5/1135; A61B 5/14551; A61B 5/742; A61B 2560/0475; G06T 11/206; G06T 2210/41; G16H 15/00; G16H 30/20; G16H 50/30; G16H 40/63
  See application file for complete search history.

(56) References Cited

U.S. PATENT DOCUMENTS

| | | | |
|---|---|---|---|
| 2005/0115561 A1* | 6/2005 | Stahmann | A61B 5/02055 128/204.23 |
| 2005/0143617 A1 | 6/2005 | Auphan | |
| 2010/0049008 A1* | 2/2010 | Doherty | A61M 16/024 128/204.23 |
| 2012/0256950 A1 | 10/2012 | Masuda | |
| 2013/0046151 A1 | 2/2013 | Bsoul et al. | |
| 2016/0080833 A1 | 3/2016 | Denoual et al. | |

FOREIGN PATENT DOCUMENTS

| | | |
|---|---|---|
| EP | 2644087 A1 | 10/2013 |
| JP | 2004097496 A | 4/2004 |
| JP | 2012014251 A | 1/2012 |
| JP | 2013208283 A | 10/2013 |
| WO | 2012168912 A1 | 12/2012 |
| WO | 2012170586 A2 | 12/2012 |

OTHER PUBLICATIONS

International Search Report and Written Opinion for Application No. PCT/AU2014/050305 dated Dec. 17, 2014.
Notice of Reasons for Rejection for Japanese Patent Application No. 2020-197836, dated Oct. 15, 2021.

* cited by examiner

Statistics

| NORMAL | MILD | MODERATE | SEVERE |
|---|---|---|---|
| 0  5 | | 15 | 30 |

602 → 1.2

| | | | | | | |
|---|---|---|---|---|---|---|
| Events index | | AHI: | 1.2 | Apnea: | 0.9 | Hypopnea: 0.3 |
| Events totals | | | | Apnea: | 6 | Hypopnea: 2 |
| Apnea index | Obstructive: 0.8 | Central: | 0.2 | Mixed: | 0.0 | Unclassified: 0.0 |
| Oxygen desaturation | | | | ODI: | 0.9 | Total: 6 |
| Oxygen saturation % | | Baseline: | 98 | Avg: | 97 | Lowest: 93 |
| Oxygen saturation – eval time % | | ≤90% sat: | 0 | ≤85% sat: | 0 | ≤80% sat: 0 |
| Breaths | | Total: | 0 | Avg/min: | 0.0 | Snores: 53 |
| Pulse - bpm | | Min: | 48 | Avg: | 57 | Max: 87 |

Analysis guidelines       AASM 2007 Automatic Scoring

Apnea[10%; 10s; 80s; 1.0s; 20%; 60%; 8%]; Hypopnea[70%; 10s; 100s; 1.0s]; Snoring[6.0%; .03s, 3.5s; 0.5s]; Desaturation[4.0%] Hypopneas were scored only if there was valid oximetry data.

Statistics

| NORMAL | MILD | MODERATE | SEVERE |
|---|---|---|---|
| 0 | 5 | 15 | 30 |

802 → 29.9

| | | | | | | |
|---|---|---|---|---|---|---|
| Events index | | AHI: | 29.9 | Apnea: | 22.6 | Hypopnea: 7.3 |
| Events totals | | | | Apnea: | 170 | Hypopnea: 55 |
| Apnea index | Obstructive: 12.8 | Central: | 9.0 | Mixed: | 0.8 | Unclassified: 0.0 |
| Oxygen desaturation | | | | ODI: | 20.4 | Total: 154 |
| Oxygen saturation % | | Baseline: | 95 | Avg: | 94 | Lowest: 87 |
| Oxygen saturation – eval time % | | ≤90% sat: | 2 | ≤85% sat: | 0 | ≤80% sat: 0 |
| Breaths | | Total: | 0 | Avg/min: | 0.0 | Snores: 1195 |
| Pulse - bpm | | Min: | 49 | Avg: | 61 | Max: 93 |

Analysis guidelines    AASM 2007 Automatic Scoring

Apnea[10%; 10s; 80s; 1.0s; 20%; 60%; 8%]; Hypopnea[70%; 10s; 100s; 1.0s]; Snoring[6.0%; .03s, 3.5s; 0.5s]; Desaturation[4.0%] Hypopneas were scored only if there was valid oximetry data.

FIG. 8

ELECTRONIC MANAGEMENT OF SLEEP RELATED DATA

CROSS-REFERENCE

This application is a continuation of U.S. patent application Ser. No. 15/031,923, filed Apr. 25, 2016, which is a national phase entry under 35 U.S.C. § 371 of International Application No. PCT/AU2014/050305, filed Oct. 24, 2014, published in English, which claims priority from Australian Provisional Application No. 2013904136, filed on Oct. 25, 2013, the disclosures of all of which are incorporated herein by reference.

FIELD OF THE INVENTION

The present technology relates to the detection and diagnosis of sleep-disordered breathing. In particular, the present technology relates to a system for the electronic management of sleep data, such as sleep related diagnostic data.

BACKGROUND OF THE TECHNOLOGY

Testing is a vital part of diagnosing patients with sleep-disordered breathing (SDB) and prescribing them for therapy on Home Medical Equipment (HME). While the diagnostic testing is traditionally performed in a sleep lab, due to its convenience and cost effectiveness, home sleep testing (HST) is rapidly becoming a dominant method of diagnosing patients with obstructive sleep apnoea (OSA). It is possible that the newly emerging home-focused diagnostic testing in time may replace a large proportion of tradition sleep lab testing.

Thus, diagnostic providers are increasingly using portable take home testing devices to diagnose patients with SDB. For example, patients suffering from sleep apnea may undergo various degrees of testing by using a devices such as the ResMed's ApneaLink® or CleveMed's SleepView home testing device. Such testing and diagnostic devices may generate sleep related data that may include one or more signal channels such as respiratory flow, respiratory pressure, respiratory ventilation, respiratory effort, oxygenation, pulse, snore etc.

The data collected by the diagnostic device may then be reviewed by a Sleep Lab physician. If some form of SDB condition is diagnosed, for example OSA, the patient may be prescribed a therapy device, such as a continuous positive airway pressure ("CPAP") device, for home respiratory therapy.

The patient's data associated with the use of the diagnostic device is uploaded to the service provider's servers. The only way for a treating physician or sleep clinician to review such data is by downloading it to their own computer, which is typically remote to the servers. Such an upload may be associated with substantial amount of time. In practice, when reviewing patient data the download of a sleep data file alone may take several minutes. This is because HST software solutions currently in the market download the entire sleep study file (e.g., an EDF+ type file) to the user's computer, before allowing any sections of the data to be viewed. The file often includes the sleep related data from several nights, with each night of sleep data itself often having a number of sleep sessions. Thus, the size of data file associated with an entire sleep test can be significant. As a result, downloading the data file on a personal computer often results in a waiting time of more than 3 minutes before a sleep physician may begin viewing and analysing the study.

The above issue is further complicated when there is a need to introduce some manual changes in the diagnostic evaluation of the sleep data. As it will be described below, sleep physicians can choose to re-evaluate diagnosed SDB events scored in the originally downloaded data file. Currently, such a change necessitates the entire amended data file to be uploaded back to the server for re-evaluation of the total sleep score. Such multiple data transfers of large sleep data files can cause unnecessary distraction and waste of time.

BRIEF SUMMARY

Aspects of the disclosure set forth a method for electronic management of sleep related information obtained by a sleep related measurement device. The method may include receiving sleep data; storing the sleep data so as to associate the sleep data with a plurality of sleep sessions; enabling a user to select for download a selected sleep session; generating a plurality of image tiles corresponding to the sleep data of the selected session; and transmitting the plurality of image tiles.

In addition, the plurality of image tiles may be transmitted so that at least a first image tile, from the plurality of image tiles, may be downloaded by a receiving computer, prior to all of the plurality of image tiles being downloaded. The method may also include automatically scoring diagnostic events based on the received sleep data. Transmitting the image tiles may include an event indicator that displays the scored diagnostic events associated with the selected sleep session, wherein each of the transmitted tiles corresponds to a time period included on the event indicator.

In accordance with another aspect, the method may include generating a report based on the sleep data and/or the scored diagnostic events. One or more script elements indicative of scored diagnostic events may also be transmitted, with one or more script elements being manually adjustable by the user. One or more script elements may be superimposed onto a respective one of the plurality of image tiles when displayed to a user.

In yet another aspect, the method may include receiving data indicative of user adjustments to one or more script elements. The automatic scoring may then be recalculated based on the received data indicative of the user adjustments to the one or more script elements.

In still another aspect, the methods described herein may be performed by a system of one or more computing devices. The one or more computing devices may one or more processors configured to perform the disclosed methods.

BRIEF DESCRIPTION OF DRAWINGS

The accompanying drawings facilitate an understanding of the various embodiments of this present technology. In such drawings:

FIG. 6 depicts a diagnostics report provided as a result of automatic scoring of sleep related events as indicated in FIG. 4, in accordance with an aspect of the disclosed technology;

FIG. 8 depicts a diagnostics report provided as a result of scoring of the edited sleep related events as indicated in FIG. 4, in accordance with an aspect of the disclosed technology;

DETAILED DESCRIPTION

The proposed technology utilizes a unique combination of streaming server-side tiling technology and optimized user interface design to allow sleep related data file to be loaded onto an electronic device as a series of images. Details of some aspects of streaming server-side tiling technology can be found in published patent documents U.S. Pat. Nos. 8,560,600 and 8,260,006. In particular, U.S. Pat. No. 8,560,600 describes details of the mechanics of a server using server data to render visual map elements such as image tiles for display of maps. U.S. Pat. No. 8,260,006 describes how mapping tiles can be linked together seamlessly to form a single display within the user's browser.

Figure 1:
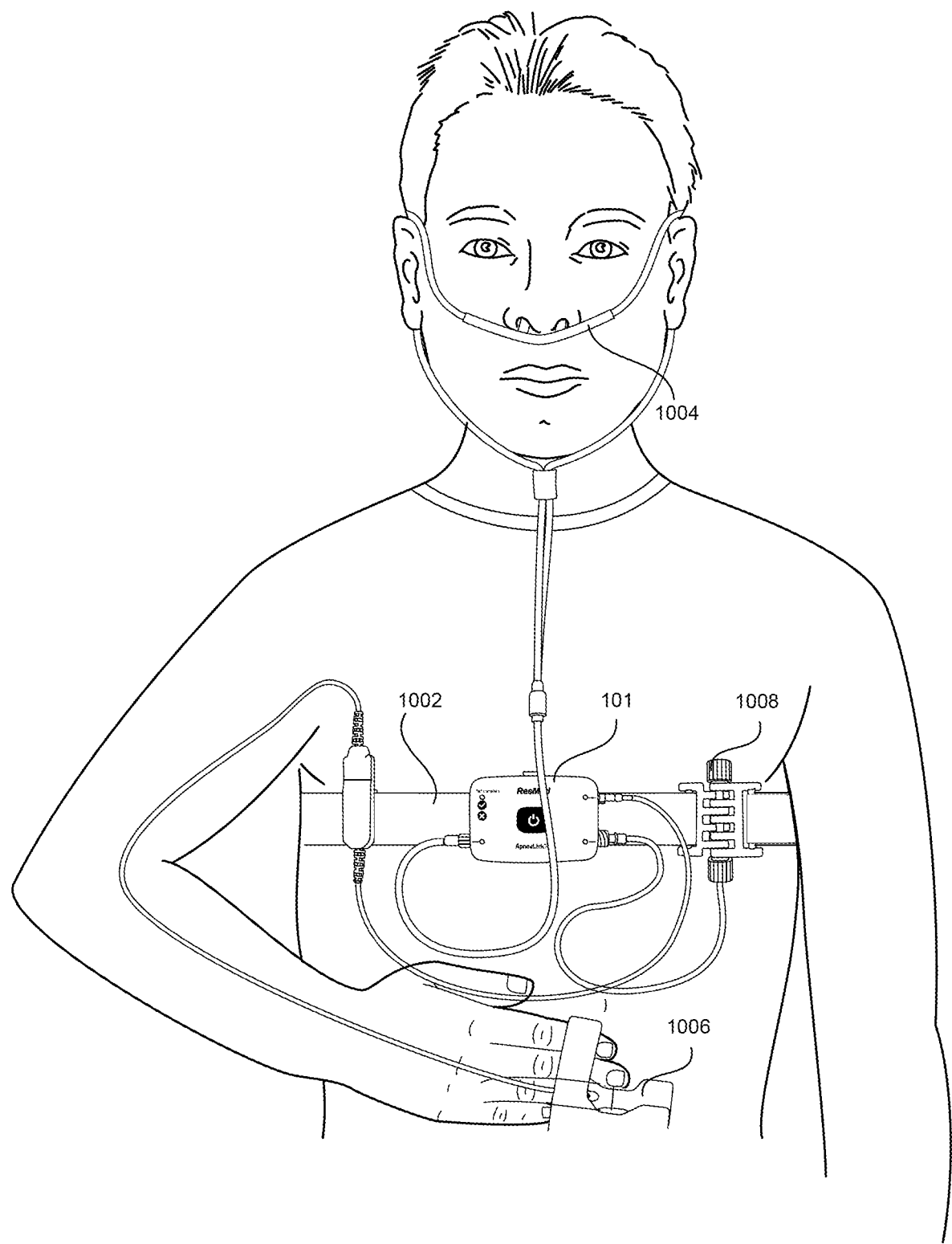
FIG. 1 depicts a diagnostic device in accordance with aspects of the disclosed technology.
Figure 2:
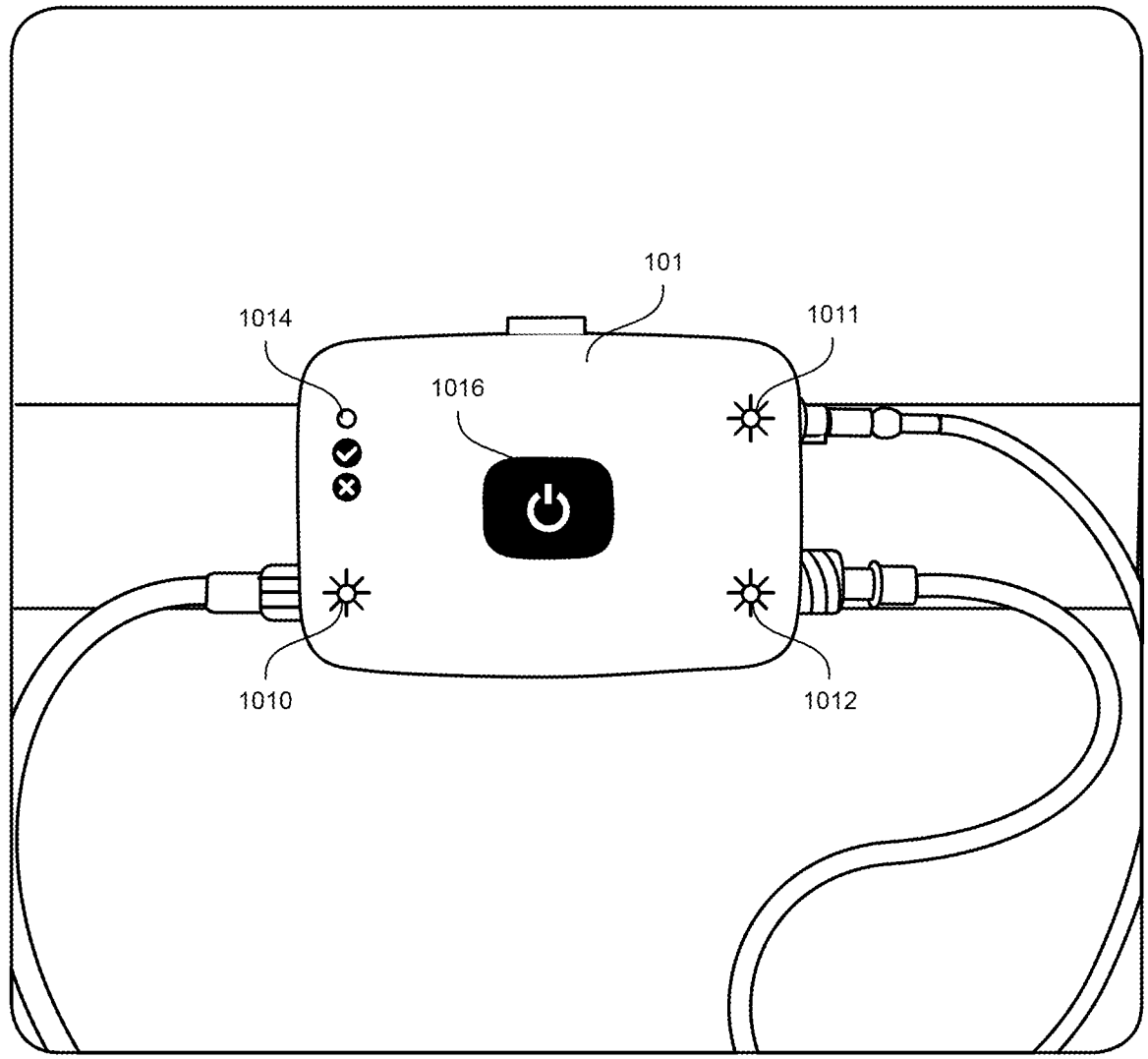
FIG. 2 depicts a diagnostic device in accordance with aspects of the disclosure technology.

FIGS. 1 and 2 show an example diagnostic device 101 that may be used by a patient to collect sleep related diagnostic data. The patient may wear diagnostic device 101 by strapping belt 1002 around his or her chest. Cannula 1004 may then be placed with respect to one or more of the patient's airway passages, such as the nasal passages, so as to measure parameters associated with the patient's breathing, such as airflow. Diagnostic device 101 may also include an oximeter sensor 1006 that may measure the patient's pulse and oximetry levels. Oximeter sensor 1006 may be worn by the patient as a finger clip. In addition, diagnostic device 101 may include an effort sensor 1008 for measuring patient's breathing effort during sleep. Effort sensor 1008 may be attached to belt 1002 in proximity to the patient's rib cage and lungs.

As shown in FIG. 2, diagnostic device 101 may include indicator lights 1010, 1011, and 1012 to indicate whether diagnostic device 101 is properly connected to cannula 1004, oximeter sensor 1006, and effort sensor 1008, respectively. For example, indicator lights 1010-12 may activate, flash, or change color if diagnostic device 101 determines that one of the sensors are not properly connected. Testing light 1014 may indicate whether a diagnostic test has been properly completed or whether an error has occurred during the diagnostic test. Diagnostic device 101 may also include user interfaces, such as power button 1016. The user interface may include an interactive display (not shown) for displaying diagnostic data and receiving user input. As discussed below, diagnostic device 101 may collect sleep test data from the patient as he or she sleeps. This data may be stored by diagnostic device 101 and transmitted to a remote computing device.

Figure 3:
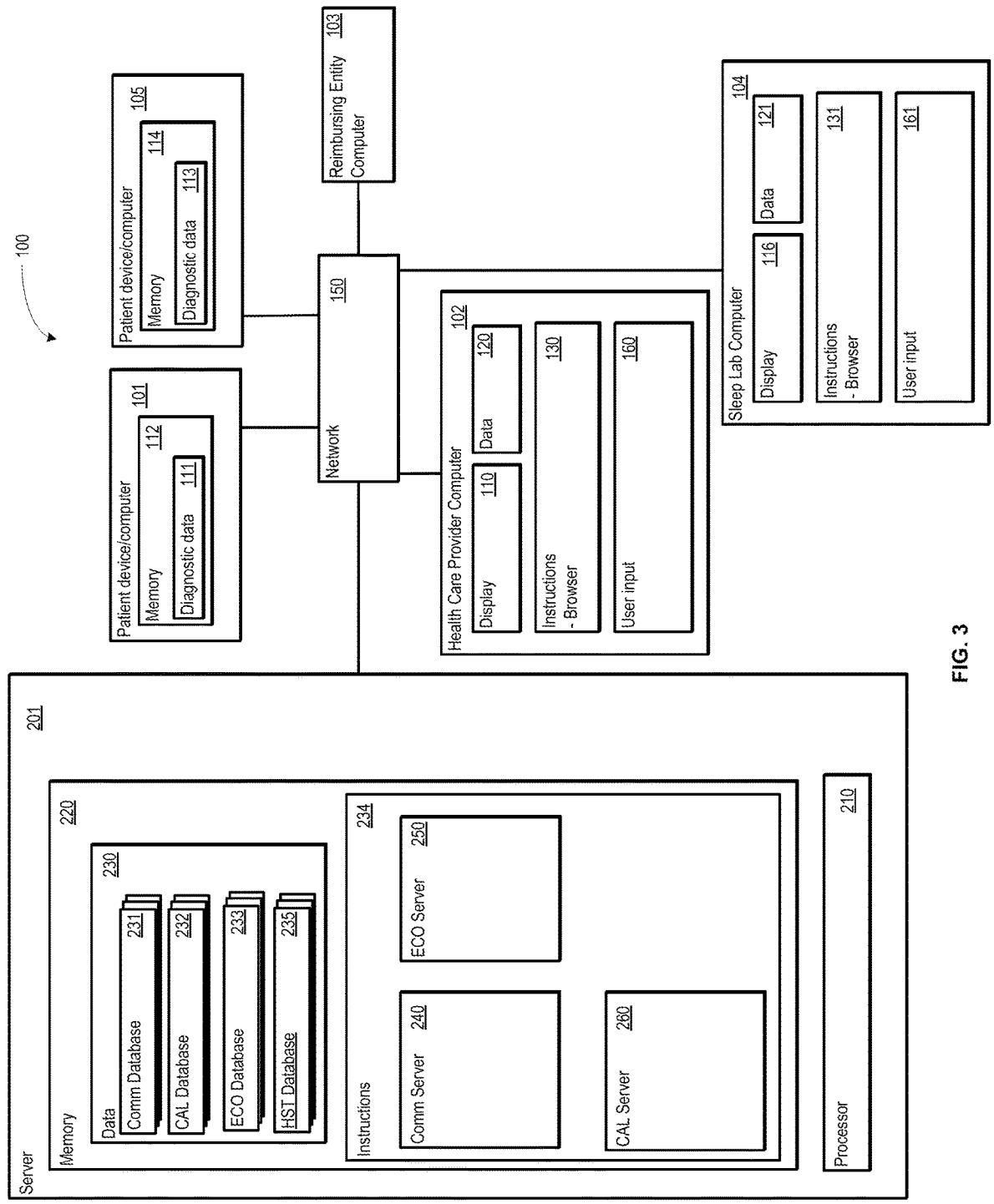
FIG. 3 depicts schematic representation of an electronic system for facilitating the method for electronic management of sleep related data in accordance with an aspect of the disclosed technology.

FIG. 3 shows an electronic system that may be implemented in connection with the present technology. As shown in FIG. 3, a system 100 includes a patient diagnostic device 101, a diagnostic provider (e.g., sleep lab) computer 104, a therapy device 105 (e.g., an RPT device), a therapy provider computer 102, and a server 201, all of which may be connected to a network 150 (the 'cloud'). The diagnostic device 101, the computing device 104 (also referred to as user's computer) and the server 201 (also referred to as service provider's server) may be located remotely with respect to each other. The diagnostic device 101 may be any home sleep testing device used by a patient. As the patient uses medical diagnostic device 101, diagnostic data 111 may be recorded on a storage medium, also referred to as memory 112. Diagnostic data 111 may include any data relating to the patient's sleep test, such as date, time, and duration of test, as well as biometric clinical information such as recorded respiratory flow data, respiratory effort data, oximetry, and pulse data. Memory 112 may be of any non-transitory type capable of storing information accessible by a processor, including a computer-readable medium, or other medium that stores data that may be read with the aid of an electronic device, such as a hard-drive, memory card, ROM, RAM, DVD or other optical disks, as well as other write-capable and read-only memories.

Server 201 may include a processor 210 and a memory 220. Memory 220 is used for storing data 230, which are accessible by processor 210, as well as instructions 234, which may be executable or otherwise usable by the processor 210. The memory 220 may be of any non-transitory type capable of storing information accessible by the processor, including a computer-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 234 may be any set of instructions to be executed directly (such as machine code) or indirectly (such as scripts) by the processor. For example, the instructions may be stored as computer code on the computer-readable medium. In that regard, the terms "instructions" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below. Instructions 234 may also contain instructions for operating one or more virtual servers, such as Communication (Comm) server 240, Easy Care Online (ECO) Server 250, and Communication Abstraction Layer (CAL) server 260.

The Communication Abstraction Layer (CAL) is responsible for communicating with Therapy Devices. The CAL's core responsibilities include, obtaining daily summary data for active patients; retrieving and changing therapy device settings; and converting raw therapy device data into an easily digestible format.

The Communications Server (Comm) is responsible for initially communicating with the wireless Therapy Devices and validating their output. The Communications Server's core responsibilities includes, communicating with Flow Generators via a Communication Module or inbuilt Communications Device; validating the incoming wireless data; and converting the wireless data into a format which can be read by the CAL server.

The ECO Server is responsible for application functionality within the system. The ECO Server's core responsibilities include presenting patient and device information within the user interface, writing and managing patient health information and running applications related to the technology. This is the server directly responsible for running the applications associated with the proposed tiling technology.

The data 230 may be retrieved, stored and/or modified by processor 210 in accordance with the instructions 234. For instance, although the system and method is not limited by any particular data structure, the data may be stored in computer registers, in a relational database as a table having a plurality of different fields and records, XML documents or flat files. The data may also be formatted in any computer-readable format. The data may comprise any information sufficient to identify the relevant information, such as numbers, descriptive text, proprietary codes, references to data stored in other areas of the same memory or different memories (including other network locations) or information that is used by a function to calculate the relevant data. Data 230 may include one or more databases, including a Comm database 231, CAL database 232, ECO database 233, and HST database 235.

The processor 210 may be any conventional processor, including commercially available processors. Alternatively, the processor may be a dedicated device such as an application specific integrated chip (ASIC) or field-programmable gate array (FPGA), for example. Although FIG. 3 functionally illustrates the processor, memory, and other elements of server 201 as being within the same block, it will be understood by those of ordinary skill in the art that the processor and memory may actually comprise multiple processors and memories that may or may not be stored within the same physical housing. For example, memory may be a hard drive or other storage media located in a housing different from that of server 201. Accordingly, references to a processor or computer will be understood to include references to a collection of processors or computers or memories that may or may not operate in parallel or even be located at the same site. Rather than using a single processor to perform the steps described herein some of the components such as steering components and deceleration components may each have their own processor that only performs calculations related to the component's specific function. Thus, server 201 may be referred to as both a system and an apparatus.

Computers 102, 103 and 104 may include all of the components normally used in connection with a computer, such as a central processing unit (CPU), memory (e.g., RAM and internal hard drives) storing data 120 and 121, instructions 130 and 131 such as a web browser, an electronic display 110 and 116 (e.g., a monitor having a screen, a small LCD touch-screen or any other electrical device that is operable to display information), and user input 160 and 161 (e.g., a mouse, keyboard, touch screen, and/or microphone).

The memory 112 may be internal to the diagnostic device 101 and may be accessed by connecting an USB data cable to a separate computer. Accordingly, the term "diagnostic device" in such a case may be interpreted broadly to include a personal computer, such as a desktop or mobile computer, which contains diagnostic data 111 collected from a medical device, such as a home sleep testing device. In addition, while FIG. 3 illustrates server 201 and devices 101-104 as being connected via a common network 150, each two or more devices within system 100 may be connected via a separate network.

In one example, ECO server 250 and ECO database 233 may reside on a device at a location that is remote from Comm server 240, Comm database 231, CAL server 260, and CAL database 232. In addition, Comm server 240, Comm database 231, CAL server 260, and CAL database 232 may exist on a single device.

A patient may use a medical diagnostic device 101 in connection with a diagnostic order prescribed by a primary care physician/general medical practitioner or by a sleep physician. As the patient uses the device, diagnostic device 101 may collect data including physiological clinical information, time and dates of usage, and any other relevant data. In this regard, although FIG. 1 illustrates a specialized diagnostic device that does not provide treatment or therapy, in some cases, a diagnostic device may also be capable of providing a therapy. Such an example diagnostic device may be a respiratory pressure therapy device, such a CPAP device, which is provided with diagnostic capabilities.

A user of system 100, such as a user of computer 104, may have a direct access to memory 112 of the medical diagnostic device 101. Alternatively, the user can connect diagnostic device 101, such as via a USB cable, to a local computer, which may then upload the data to the server 201, or may allow the computer 104 to access the data of internal memory 112. A web browser 131 on the computer 104 may then be used to contact server 201 and upload diagnostic data 111 to one or more of the server's databases. Alternatively, the diagnostic device 101 may include a Bluetooth or Wi-Fi transmission capabilities and the diagnostic data may be uploaded directly from the diagnostic device 101 to the server 201 wirelessly.

The diagnostic data 111 provided to server 201 from diagnostic device 101 may be stored in the HST database 235. For example, each diagnostic device 101 may be assigned a device ID, which is provided to server 201 along with the diagnostic data. The diagnostic data may then be stored by server 201 in a database that uses the device ID to associate the received data with the appropriate patient diagnostic device 101.

In some instances, a patient is required to use a medical diagnostic device for a set duration and exhibit certain clinical symptoms in order to be eligible to qualify for therapy. For example, a patient who has been ordered a home sleep test will often be required to use the diagnostic device for at least four hours and exhibit an Apnea-Hypopnea Index (AHI) of greater than 5 in order for a physician to write a prescription for CPAP therapy. System 100 may then be used to track whether the patient has been compliant in using the diagnostic device and may assist a physician in making a diagnosis.

A sleep data file covering one or more sleep sessions may be uploaded from a diagnostic device 101 to a remote server, such as by being uploaded to the HST database of server 201 shown in FIG. 3. The sleep data file may be in an EDF+ format and may include built-in delineators that indicate the beginning and the end of sleep sessions within the file. An individual sleep session may be defined by a predetermined time period or a predetermined set of testing conditions. In particular, a sleep session may correspond to the time period in which the patient has experienced a period of continuous or near-continuous sleep. For example, if the patient slept uninterruptedly from 12:15 AM to 7:30 AM, that period of time may be defined as a single sleep session. A sleep session may also be based on some predetermined period of time in which sleep data was collected. For example, a sleep session may be defined by a four-hour period of time in which sleep data was collected.

The delineators within the sleep data file allow for the identification of separate sleep sessions, as well as for the selection and extraction of a specific session for download. The sleep data may include a plurality of separate data channels corresponding to the various diagnostic sensor data collected by diagnostic device 101. For example, a sleep data file may include data from five separate data channels corresponding to measurements of the patient's air flow, respiratory effort, oxygen saturation, pulse, and snoring.

When the sleep data is uploaded onto the server 201, a software analyser may run at the server to autoscore pre-defined events, such as SDB events (e.g., apnea, hypopnea), oxygen desaturation events, etc. The scoring comprises associating specific sleep data, such as flow or oxygen desaturation data, with specific sleep events, such as apnea, hypopnea, etc. The scoring is based on predetermined algorithms programmed in the analyser. The analyser may also generate a report, such as the one that will be discussed later in the text in relation to FIG. 6. The report may include a statistical summary of the data itself and/or of events scored on the basis of the uploaded data. The report of a specific sleep session may be displayed to the user when a session is selected. The report for the largest sleep session for a given night may also be displayed as a default report for the respective date, assuming that the user will be most interested in this session.

A sleep session may be selected in many ways. In one example, a user (e.g., a Sleep Lab Physician) may choose a date and view the available sleep sessions for that date. He or she may then choose a sleep session for that date based on one or more criteria, such as the duration of the available sessions. For example, the user may choose the longest session for a particular period of time. When a particular session is selected for download, say at a Sleep Lab Physician's computer 104, the server 201 may read the selected session data from the sleep study file and convert the data from the five signal channels into a series of bitmap image files (tiles), which the user's browser downloads. Whilst the original data may be in an EDF+ format, these tiles can be in any one of various image formats, such as GIF, BMP, PNG, etc. The download of the images is typically in a time-lapse sequence from left to right. However, this does not have to be the case and in the general case the images may be downloaded in any order. Each image that is to be displayed to the user is based on data from the sleep file, as well as additional markers of identified SDB events (also referred to in this specification as diagnostic events). Markers for other events that a data analyser at the server has been configured to score automatically based on the provided sleep data, may also be included in the displayed image. Each image corresponds to a predetermined length of time and together the combined images represent the entire selected session.

If the user selects a sleep session of, for example, five hours of length within a file for review, the session may be rendered into thirty 10-minute long images, also referred to as image tiles, each representing a sequential part of the session. The time represented by each of these images may vary. For example, the images may vary between 1 minute or less to 1 hour or more. A default image time period between 5 and 30 minutes may be set for certain forms of data review. A web browser at the user electronic device, such as computing device 104 in FIG. 3, may compile what is displayed on the user electronic device interface from a number of image elements downloaded from server 201. One or more HTML files, corresponding to at least some of the image tiles, may also be generated at the server 201 based on the original sleep data. The one or more HTML files include scripts, such as Java scripts, indicative of any SDB events requiring highlighting on the signal channels.

A special signal bitmap image tile may be generated at server 201 on the basis of the information for the entire session. This tile may be used to visualise a time line that corresponds to a time period covered by the downloaded tiles. Thus, one or more of the remaining tiles may correspond to a time period included on this tile. This specific image tile may include visualisation of one or more channels of signal data, as well as an indication of various SDB events through the session. The tile may be referred to as an event indicator. The event indicator may be downloaded to computing device 104 simultaneously with the data channel image tiles. As the event indicator may be the first tile to be downloaded, it can be clicked on by the user to adjust the view/display to specific points of interest within the displayed session. This allows the user to view specific sections of the data with increased resolution, effectively providing a zoomed view of the respective section.

Figure 4:
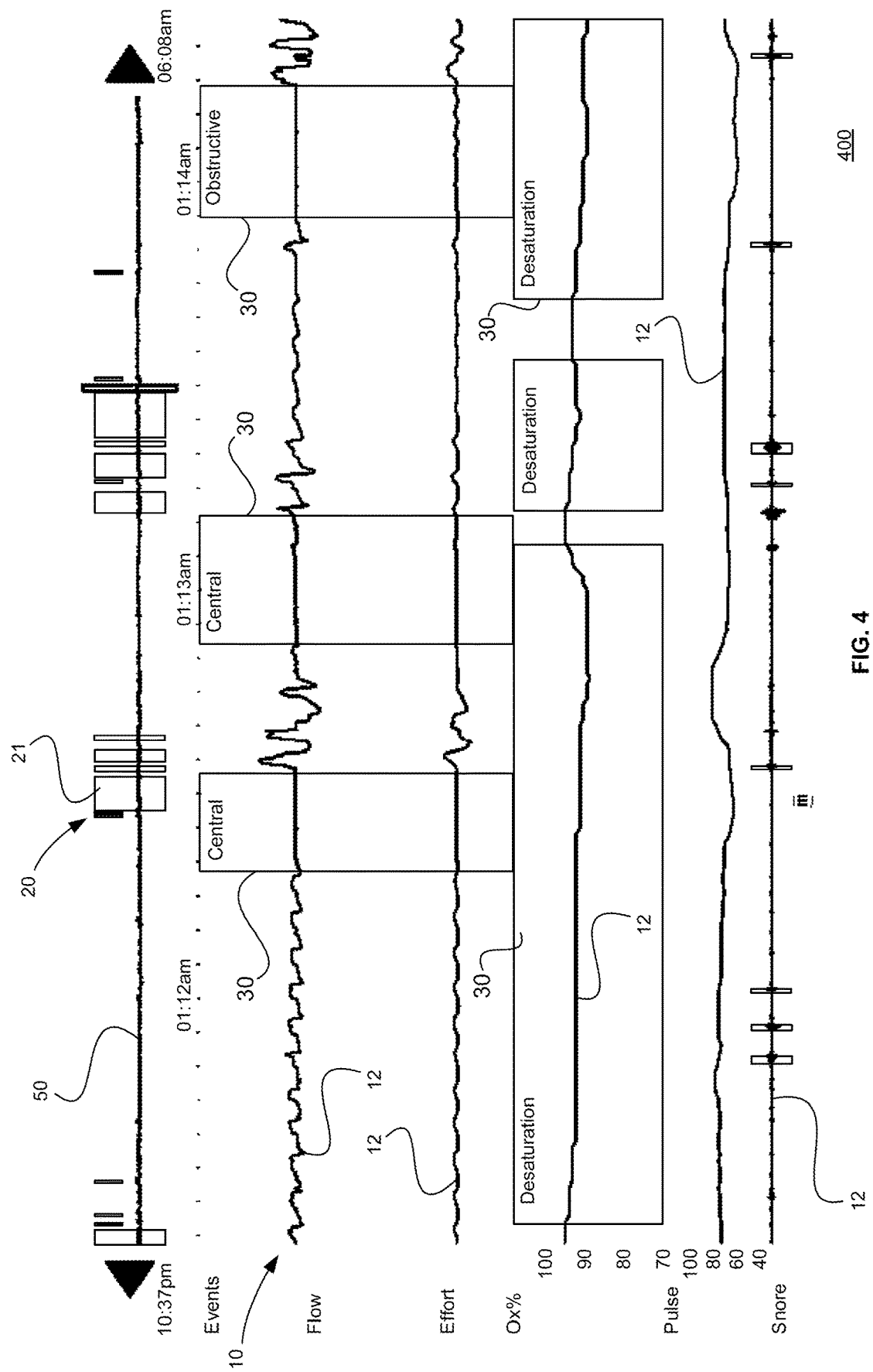
FIG. 4 depicts a visual representation of a patient's sleep related data provided to a user on a screen of the User's electronic device in accordance with an aspect of the disclosed technology.

An example screenshot 400 of a diagnostic session that may be displayed to the user can be seen in FIG. 4. Screenshot 400 displays a combination of a single image tile 10, an event indicator 20, and various superimposed JavaScript elements 30. The image tile 10 includes depictions 12 for five separate data channels, which correspond to measurements of the patient's air flow, patient's respiratory effort, oxygen saturation, pulse and snore. Data channel depictions 12 are based on the underlying diagnostic data that was collected by diagnostic device 101. JavaScript elements 30 are indications of SDB events that may have been identified automatically at the server 201 based on processing of the received sleep data from the one or more diagnostic channels. The identification of such SDB events may also be referred to as scoring. The elements 30 are displayed by the browser at the user's computing device 104 on the basis of scripts included in the HTML file downloaded together with the image tiles. Elements 30 may be superimposed onto a respective image tile 10 so as to indicate when a potentially significant SDB event has occurred in connection with a displayed one or more data channels. For example, JavaScript elements 30 have been superimposed onto the data channel depictions 12 of the patient's air flow and respiratory effort, so as to identify events 30 of central and obstructive sleep apnea. Similarly, as shown in FIG. 4, JavaScript elements 30 have been superimposed onto the patient's oximetry data so as to indicate events of oxygen desaturation. It is noted that although elements 30 are described as JavaScript elements, other scripting or processor control elements may be implemented in addition to, or as an alternative to JavaScript in some versions of the present technology. Such alternatives may include HTML5 protocol, cascading style sheets (CSS), etc.

The top of screenshot 400 displays event indicator 20, which is associated with the entire sleep session. In the illustrated example the sleep session spans from 10:37 pm to 06:08 am. The event indicator 20 may also identify instances of scored SDB events that have occurred during the sleep session. In particular, box 21 may identify when SDB, such as central sleep apnea, has occurred.

As seen in FIG. 4, screenshot 400 displays an event indicator 20 of a session that corresponds to a time period between 10:37 PM and 6:08 AM. This time period may be treated by the disclosed system as a single session or as part of a session. A user viewing screenshot 400 may select a portion of event indicator 20 to view a particular time period within the session. One or more image tiles corresponding to the selected time period may then be displayed to the user. For example, screenshot 400 shows an image tile 10 that corresponds to a time period between 1:11 AM and 1:14 AM. The relative location of the displayed tile in relation to the entire sleep session may be shown on the event indicator, as indicated by frame 701 located within the event indicator bar in FIG. 7. In this way, event indicator 20 may be used to show a summary of the patient's sleep session, while allowing a user to also quickly navigate to one or more time periods within the session, so as to view detailed data in connection with one or more data channels. Event indicator 20 may also display data relating to the patient's sleep session. For example, event indicator 20 of FIG. 4 shows oxygen saturation data 50. When viewing a particular sleep session, the data included in event indicator 20 may be the only data set preloaded onto the user's display so as to always be viewed in its entirety.

Figure 5:
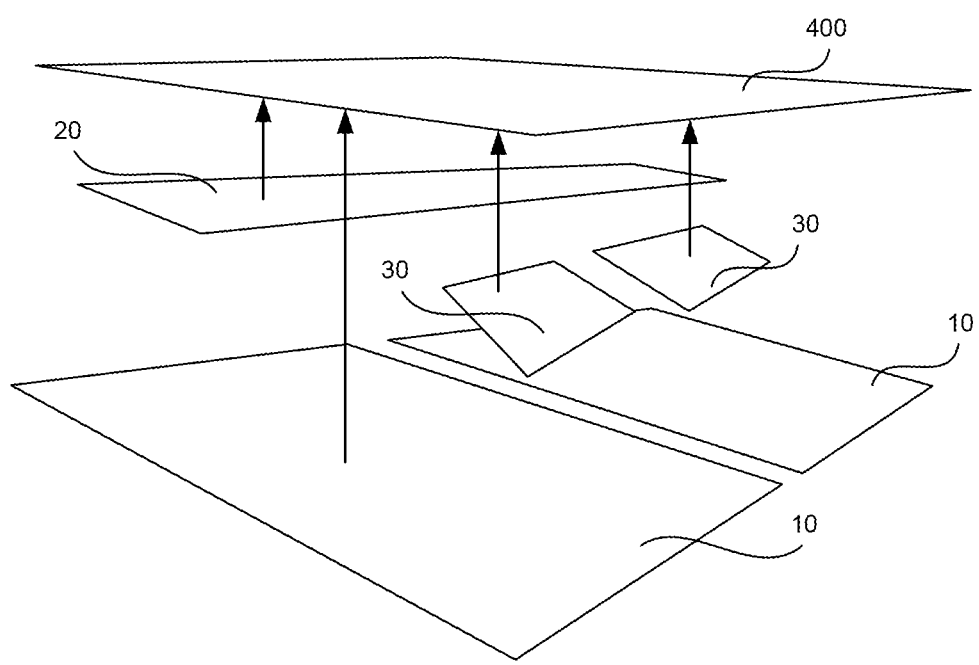
FIG. 5 depicts a schematic representation of selected functionalities of a method for electronic management of sleep related data in accordance with an aspect of the disclosed technology.

FIG. 5 shows how the event indicator 20, image tiles 10 and JavaScript elements 30 may be combined by the disclosed system to produce the webpage shown in screenshot 400. As described above, the event indicator 20 and image tiles 10 will correspond to a sleep session that has been selected by a user. A particular period of time within event indicator 20 may then be selected by the user, for which a corresponding one or more image tiles 10 and corresponding JavaScript elements 30 are selected and combined to generate the displayed webpage. In particular, once an image tile 10 is downloaded onto computing device 104, the processor of computing device 104 may read an associated HTML file and detect if there are any marked SDB events requiring highlighting on the signal channels. If such an event is identified, and it falls within the time interval being currently displayed on the web browser, the processor may prompt the web browser to render JavaScript elements 30 in a that is displayed above the image tiles, as shown in FIG. 5. As a user moves through the images of the session, the processor updates the computing device display 116 to render more JavaScript elements according to which part of the study is being viewed and may unload elements which are no longer being viewed, so as to maintain efficient use of the computing device's memory.

The manner in which the sleep related data file is downloaded from server 201 to computing device 104 allows for efficient time and data management when reviewing the data file. In particular, the disclosed system does not require an entire data file to be downloaded, thus reducing substantially the sleep physician's download time. With the proposed technology, large sleep data files may be transferred to the ECO server 250 well in advance of the time when the user attempts to access them. The much smaller image tiles 10 may be generated on demand, based on a selected sleep session data that is read from the sleep data file. The fact that the images tiles are generally substantially smaller in size than the original data and that the download is executed one tile at a time, facilitates much shorter download times (typically less than 10-30 seconds). The user may start reviewing study data substantially instantaneously, once the first image tile 10 is downloaded. Furthermore, after the download of the event indicator, which may be transmitted to be the first downloaded tile, the user is able to immediately select a time slot of interest. Once the user has chosen a particular time of interest, the respective one or more image tiles may be immediately and preferentially downloaded, allowing the user to start reviewing the time slot of interest substantially instantaneously.

As was discussed above, SDB events may be auto-scored at the server 201. Based on the raw sleep data and/or the scored sleep events, an analyser at the server 201 may also generate a report, shown by screenshot 600 in FIG. 6. This specific report may include a statistical summary of various measured parameters, such as pulse, breaths, oxygen desaturation, Apnoea and Hypopnea indices. Summary of the autoscored events, such as Apneas (6), hypopneas (2), oxygen desaturation events (6) etc. may also be displayed. This type of patient's sleep diagnostic statistics may be displayed to a user of computing device 104. A total diagnostic score, which in this case is represented by the Apnoea-Hypopnea Index 602, is automatically calculated (scored), based on the SDB diagnostic events automatically scored by the analyzer for the respective one or more sleep sessions. The AHI 602 is in this case 1.2, indicating that the patient has not suffered from SDB.

Figure 7:
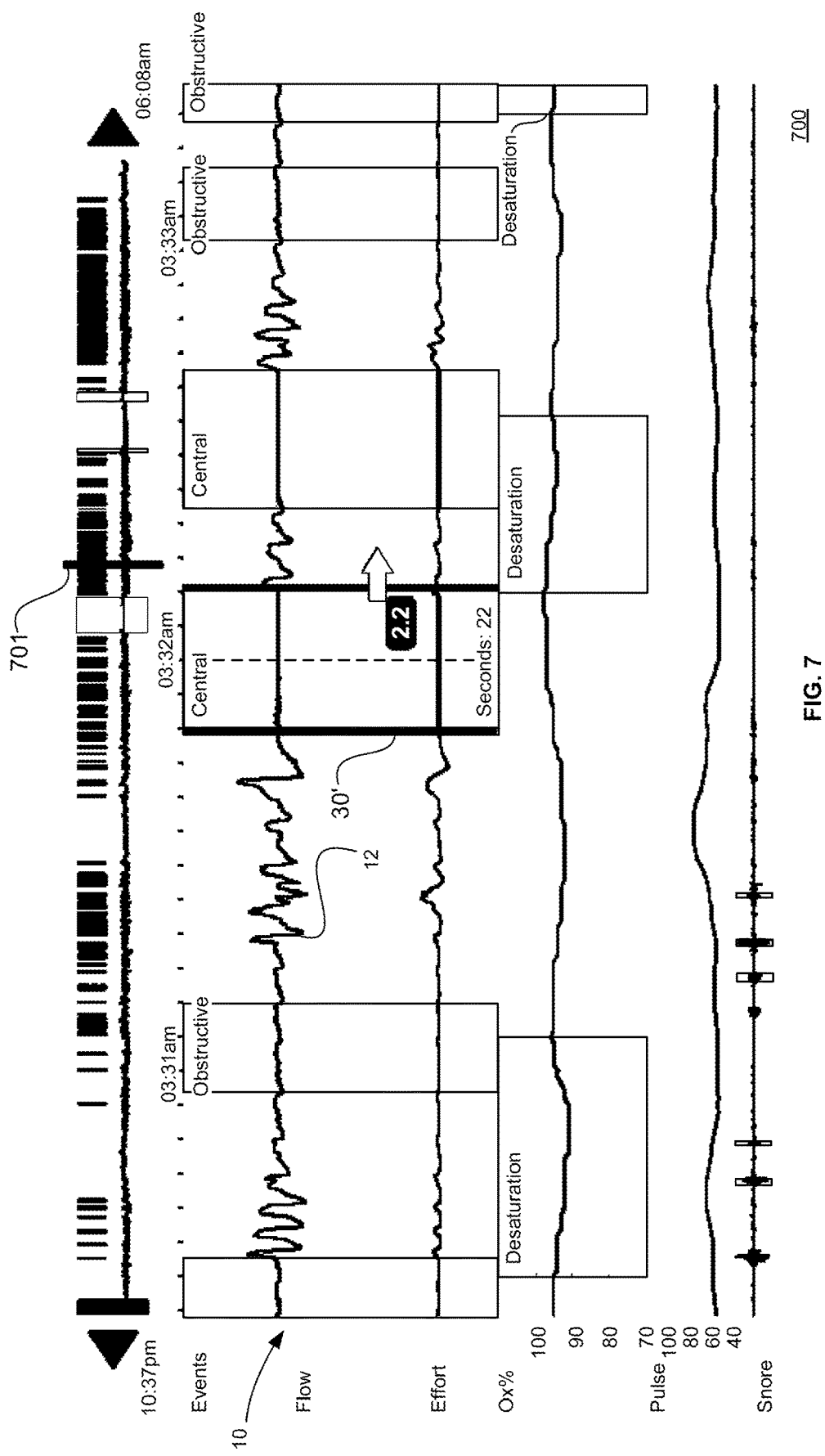
FIG. 7 depicts the visual representation of FIG. 4, wherein the automatically generated marking of some sleep related events has been edited by the user.

A sleep session may also be manually scored directly from the browser that is running on computing device 104. The manual scoring may be performed by a user of computing device 104 adjusting the size and number of JavaScript elements 30 displayed within one or more image tiles 10. For example, FIG. 7 shows screenshot 700 in which a user is adding JavaScript element 30' to image tile 10. The addition of JavaScript element 30' may be performed by the user selecting a particular point along one or more of the data channel depictions 12 using a cursor and then dragging the cursor along the selected channel depiction 12 so that the generated JavaScript element 30' corresponds to the desired period of time. A user may also select existing JavaScript elements so that they may be reshaped or deleted by the user. In this way, the user may perform a re-evaluation of the patient's auto-score. Upon completion of the re-evaluation, the patient's diagnostic statistics may be recalculated based on the modified placement of the JavaScript elements 30.

For example, as was mentioned above, an AHI auto-score of 1.2 was calculated in the report shown in FIG. 6, indicating a negative diagnosis for OSA. However, upon reviewing the raw data illustrated by the different channel signals, a sleep physician user may decide to override the auto-score manually by introducing changes to the autoscored diagnostic events, as shown in FIG. 7.

Once satisfied with the accuracy of the identified SDB events, the user may save the amended session and data indicative of the introduced changes may be sent from computing device 104 to server 201. The server 201 may recalculate the patient's diagnostic statistics based on the manual amendments introduced to the java script elements 30. As can be seen in FIG. 8, the report statistics have been updated according to the manually adjusted diagnostic events. The patient's manually adjusted SDB score (the AHI score 802) has been recalculated to be 29.9. This manually adjusted AHI score 802 now indicates that the patient has OSA. Thus, a qualified clinician may choose to override the auto-score algorithm to affect the outcome of the diagnosis. Based on the manual scores and the recalculated total SDB score, a new updated report may be generated and provided to the user's browser so as to be presented to the user.

Figure 9:
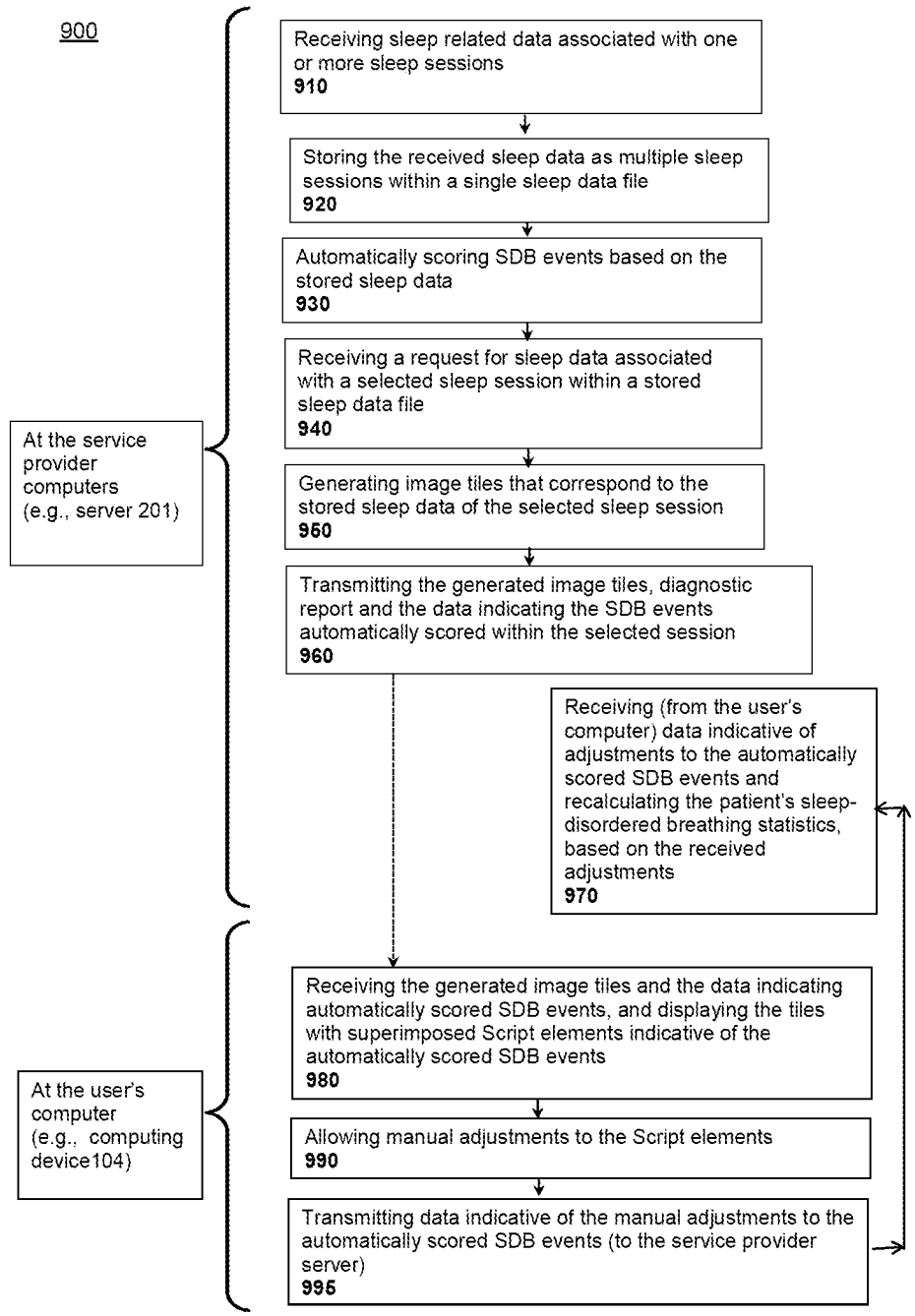
FIG. 9 is a flow diagram that may be performed in accordance with aspects of the disclosed technology.

FIG. 9 shows flow diagram 900 of a process associated with the described technology. Portions of the process may be performed by various parts of system 100 of FIG. 3, in accordance with aspects of the technology set forth above. In block 910, sleep related physiological data is received from a diagnostic device 101. The received sleep data may be diagnostic data including one or more of the data types discussed in relation to FIGS. 1 and 2 and may be associated with one or more sleep sessions. For example, the sleep data may have been collected over a period of one or more nights. In block 920, the received sleep data may be associated with a particular data file and stored as one or more sleep sessions delineated within the data file. The data may be received by an electronic device, such as the server 201, and stored in memory, such as in the HST database 235 of memory 220.

As described above, apart from the sleep data itself, the sleep data file may contain delineators that identify different sessions within the sleep data file. As shown in block 930, an automatic data analyzer at the server 201 may be configured to automatically score various SDB events identified on the basis of the received sleep related data. Such events then may become a part of the user's SDB statistics. For example, based on these automatically scored events, an overall SDB score may be allocated to the patient. The sleep data file, or an associated paired file, may include data associated with SDB event data indicators generated during the autoscoring. In block 940, a request is received for sleep data that is associated with a particular sleep session. For example, a user of computing device 104 may request that server 201 provide sleep data associated with a particular sleep data file of a particular user, which was taken on a particular date. Based on the received request, the sleep data from the selected session may generate one or more image tiles (block 950). As described above, one or more image tiles may be generated for a single session, and each image tile may contain data from multiple data channels. The generated image tiles are then transmitted to the requesting computing device (block 960). The data indicating the SDB events automatically scored within the selected session may also be transmitted, possibly as a script (such as Java script) within an HTML file that is used by the browser of the receiving computer (e.g. computing device 104) to display the tiles. The image tiles may be transmitted and displayed in a manner so that a user may begin to view at computing device 104 one or more of the tiles immediately upon the download of these specific one or more tiles, and prior to all of the image tiles being transmitted by server 201.

The requesting computing device (e.g., computer 104) may receive the transmitted image tiles and the HTML file with the scripts indicating automatically scored SDB events. The computing device 104 may then display both the tiles and their respective script elements indicative of the automatically scored SDB events (block 980). The superimposed JavaScript elements are superimposed onto the image tile so as to correspond to locations wherein a diagnostic event has supposedly occurred. The identification of the diagnostic event may be based on an analysis, by server 201, of the underlying data within the image tile. For example, based on air flow data, periods of OSA may be identified. JavaScript elements may be superimposed onto the air flow data shown in an image tile, so as to indicate the time periods in which the respective identified OSA events occurred.

The overall patient's SDB statistic and/or condition may be scored based on the identified diagnostic events (block 970). For example, server 201 may provide an AHI autoscore based on the SDB events scored during one or more sleep sessions. As described above, the user of computing device 104 may adjust the JavaScript elements that are displayed with the image tiles (block 990). This adjustment may add, remove, or otherwise change various JavaScript elements. Data indicative of this manual change to the scored SDB events may be then transferred from the user's computing device 104 to the server 201 (block 995). Upon receipt of the data indicative of the adjustments to the JavaScript elements, server 201 may recalculate the patient's SDB score based on the received manually adjustments (block 970).

In the above description, it should be noted that some of the blocks, such as 910-970, may be performed at server 201, while the remaining steps may be performed at a user electronic device, such as computing device 104. Also, the disclosed methods do not require that each of the blocks shown in flow diagram 900 be performed, nor must they be performed in the order displayed. Additional blocks may also be added to flow diagram 900 in accordance with the disclosed methods.

The proposed sleep related data processing method may run natively within the user's web-browser. This is beneficial to the service provider, because it avoids the complications associated with of their software having to be compatible with any one of a number of client-side applications. For the user of computing device 104, it provides simplicity, as it avoids the need to install and maintain dedicated software. Since no third party plug-ins are required, the application may also perform quickly and reliably. The application may be run not only on PCs, but also on tablets, smart phones and other mobile devices.

An Additional problem with currently used data processing and visualisation applications is that they are reliant on $3^{rd}$ party plugins (e.g. Java applet versions) for viewing the data at the client side. Such dependence can make their performance unpredictable, due to possible deficiencies in the third party plugins and unpredictable version updates. Current applications are also suitable only for operation on a PC.

In the disclosed method, the workload may be shifted from the processor of the local user's computing device onto the processors of the remote servers, giving the local electronic device more control over the user experience and reducing dependency on the capabilities of the client's computer/browser. This results in a more efficient method of data management and a highly responsive user experience. The approach effectively transforms a difficult to control problem, such as having to consider the capabilities of client machines in dealing with high resolution browser data and variations in Java applet versions, into a problem that can be efficiently managed, such as by processing the large sleep files using the service provider's substantial server computational capacity. This results in simplified testing, faster development, and a more consistent user experience in the final product.

The improved efficiency of the technology allows efficient processing of high volume sleep study data (e.g. 8 Million data points for a 10 hr study can be displayed in approximately 10-30 seconds).

In addition, the proposed technology, such as with processor control instructions, brings the following potential advantages:

The ability to display a sleep related study data natively within a web browser as a series of individual bitmap images.

Time efficiency—a user can start reviewing one or more of the images substantially instantaneously and well before a transmission of all bitmap images being complete.

The diagnostic events are conveniently displayed via a single line study events bar (e.g., Event Indicator).

The ability to select for download, within a large sleep data file, individual sleep sessions of a diagnostic recording on demand (e.g., if several nights of data were recorded the browser will only load the specific selected night of data that the user has selected for viewing).

The ability to view a summary of a sleep session and to quickly navigate to specific portions of the sleep session using the presented summary.

The ability to manually edit sleep study markers using JavaScript elements within a web browser.

The ability to resend data indicative of the change imparted to the edited elements to the cloud, where the sleep study statistic (also score) is recalculated based on the changes. All of the recalculations, updates, and data transfer are much more efficient as they are performed without the need of downloading large sleep data files from the server to the user's computer and without the need of uploading amended data files from the user's computer back to the server. In one example, only data indicative of the change to the SDB events indicators is sent back to the server.

A convenient visualisation of all SDB events for the entire session is provided by way of a single line study events bar (Events Indicator).

While the disclosed technology has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the disclosed technology. Also, the various embodiments, e.g., aspects of one embodiment may be combined with aspects of another embodiment to realize yet other embodiments.

For example, instead of using the user's electronic device browser to download sleep data related image tiles generated at the remote server, an alternative method may involve reproducing both the sleep data and the SDB event data at the user's computing device 104 by way of HTML, files with embedded java scripts. Such a method may utilize a third party JavaScript charting library, such as "JFreeChart", to allow for the download of HTML and JavaScript elements to the user's electronic device to display the various signal channels and the clinical markets in the device's browser.

Upon a user selecting a session to view, the server application may read the selected session from the sleep study file (EDF+ format) and convert the signal data and the automatically generated clinical markers into a series of data points which are loaded into the JavaScript charting library. This library in turn converts the points to an array of HTML and JavaScript elements which are downloaded to the user's browser and displayed as images. Thus, the method can be used with different download mechanisms.

The method is also flexible as to the type of sleep data to which it is applicable. While the method has been illustrated with reference to sleep data and, more specifically to specific data channels illustrated in FIGS. 4 and 7, it is to be understood that the method may be used with other sleep-related data. For example, data detected and/or generated by various contact-less sleep monitors, such as SleepMinder™ or the like, can also be downloaded in similar manner. Such data may include, but is not limited to, detected sleep stages, patient's temperature, heart rate, blood pressure, breathing rate, snoring, environmental parameters, such as sound, temperature, light level etc. Accordingly, the scored events 30 may not be SDB events, as discussed in the above description, but other type of events that are associated with the specific type of sleep data used.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously. It is therefore to be understood that numerous modifications may be made to the illustrative embodiments and that other arrangements may be devised without departing from the spirit and scope of the technology.

Also, the various embodiments described above may be implemented in conjunction with other embodiments, e.g., aspects of one embodiment may be combined with aspects of another embodiment to realize yet other embodiments. In addition, while the technology has particular application to sleep related data and diagnostic data associated with patients suffering from OSA and other SDB, it is to be appreciated that patients suffering from other illnesses (e.g. congestive heart failure, morbid obesity, stoke, bariatric surgery, etc.) can derive benefit from the above teachings. Moreover, the above teachings have applicability with patients and non-patients alike in non-medical applications.

Glossary

Air: Air will be taken to include breathable gases, for example air with supplemental oxygen.

Auto-scoring: The automated process where a custom algorithm analyzes the sleep study's raw data and marks up/highlights areas where the algorithm detects occurring clinically significant SDB events Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

European Data Format (EDF+): A standard file format designed for exchange and storage of medical time series. It is the native file which most diagnostic devices, including the ApneaLink, record into. The file can contain multiple nights/sessions of sleep data as well as markers of SDB events.

Interpretation: The process by which a Sleep Physician views results from a sleep study and makes a clinical diagnosis in regards to whether a patient requires therapy for further testing.

Manual Scoring: The process of looking at a sleep study's raw data and manually marking up/highlighting areas where the user believes significant SDB events are occurring to the patient.

Re-analyze/Re-calculate: The process of taking new input data generated from a manual score or a change of parameters and feeding it back into analyzer to produce new clinical statistics, such as AHI.

Sleep physician: A physician certified by the board of the American Association of Sleep Medicine as legally qualified to give a diagnosis for various Sleep Disordered Breathing conditions.

Obstructive Sleep Apnea (OSA): A form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR): A form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS): The combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD): Encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD): A term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hyperpnea: An increase in flow to a level higher than normal flow rate.

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

The invention claimed is:

1. A method for electronic management of sleep related information obtained by a sleep related measurement device, the method comprising:
   receiving, by one or more processors, sleep data comprising data from a plurality of sensors;
   storing, by the one or more processors, the sleep data so as to associate the sleep data with a plurality of sleep sessions;
   enabling, by the one or more processors, a user to select for download a selected sleep session;
   generating, by the one or more processors, a plurality of image tiles corresponding to the sleep data of the selected sleep session;
   generating, by the one or more processors, at least one script element indicative of a diagnostic event associated with the sleep data, the at least one script element is configured to, when displayed to the user, be: (a) displayed in association with a portion of the sleep data depicted in at least one of the plurality of image tiles to indicate when the diagnostic event occurred in connection with the depicted sleep data, and (b) manually adjustable by the user within a display environment relative to the depicted sleep data; and
   transmitting, by the one or more processors, the plurality of image tiles and the at least one script element.

2. The method of claim 1, further comprising receiving, by the one or more processors, data indicative of at least one user adjustment to the at least one script element within the display environment.

3. The method of claim 2, wherein the at least one user adjustment comprises changing a size or position of the at least one script element within the display environment.

4. The method of claim 2, wherein the at least one user adjustment comprises deleting the at least one script element within the display environment.

5. The method of claim 2, further comprising automatically scoring, by the one or more processors, diagnostic events, based on the received sleep data.

6. The method of claim 5, further comprising:
   generating, by the one or more processors, an event indicator that identifies scored diagnostic events occurring during the selected sleep session; and
   transmitting, by the one or more processors, the event indicator.

7. The method of claim 6, wherein each image tile of the plurality of image tiles represents sleep data for a separate time period included in the event indicator.

8. The method of claim 5, further comprising generating, by the one or more processors, a report based on at least one of the sleep data and the scored diagnostic events.

9. The method of claim 8, further comprising recalculating, by the one or more processors, the report based on the received data indicative of the user adjustment to the at least one script element.

10. The method of claim 5, further comprising receiving, by the one or more processors, data indicating that the user has added at least one second script element to the at least one image tile.

11. The method of claim 10, further comprising, recalculating, by the one or more processors, a report based on the received data indicating that the user added the at least one second script element to the at least one image tile, the report being based on at least one of the sleep data and the scored diagnostic events.

12. The method of claim 1, wherein the sleep data comprises a plurality of signal channels, each signal channel associated with a different type of sleep data, and wherein the generating of the plurality of image tiles comprises converting the sleep data from the plurality of signal channels into bitmap image tiles.

13. A system for electronic management of sleep related information obtained by a sleep related measurement device, the system comprising:
   a memory for storing sleep data comprising data from a plurality of sensors; and
   one or more processors in connection with the memory, the one or more processors configured for:
   storing the sleep data so as to associate the sleep data with a plurality of sleep sessions;
   enabling a user to select for download a selected sleep session;
   generating a plurality of image tiles corresponding to the sleep data of the selected sleep session;
   generating at least one script element indicative of a diagnostic event associated with the sleep data, the at least one script element is configured to, when displayed to the user, be: (a) displayed in association with a portion of the sleep data depicted in at least one of the plurality of image tiles to indicate when the diagnostic event occurred in connection with the depicted sleep data, and (b) manually adjustable by the user within a display environment relative to the depicted sleep data; and transmitting the plurality of image tiles and the at least one script element.

14. The system of claim 13, further comprising receiving, by the one or more processors, data indicative of at least one user adjustment to the at least one script element within the display environment.

15. The system of claim 14, wherein the at least one user adjustment comprises changing a size of the at least one script element within the display environment.

16. The system of claim 14, wherein the at least one user adjustment comprises deleting the at least one script element within the display environment.

17. The system of claim 14, further comprising automatically scoring, by the one or more processors, diagnostic events, based on the received sleep data.

18. The system of claim 17, wherein the one or more processors are further configured to generate an event indicator that identifies scored diagnostic events occurring during the selected sleep session and transmit the event indicator.

19. The system of claim 18, wherein each image tile of the plurality of image tiles represents sleep data for a separate time period included in the event indicator.

20. The system of claim 17, wherein the one or more processors are further configured to generate a report based on at least one of the sleep data and the scored diagnostic events.

21. The system of claim 20, wherein the one or more processors are further configured to recalculate the report based on the received data indicative of the user adjustment to the at least one script element.

22. The system of claim 17, wherein the one or more processors are further configured to receive the data indicating that the user has added at least one second script element to the at least one image tile.

23. The system of claim 22, wherein the one or more processors are further configured to recalculate a report based on the received data indicating that the user added the at least one second script element to the at least one image tile, the report being based on at least one of the sleep data and the scored diagnostic events.

24. The system of claim 13, wherein the sleep data comprises a plurality of signal channels, each signal channel associated with a different type of sleep data, and wherein the generating of the plurality of image tiles comprises converting the sleep data from the plurality of signal channels into bitmap image tiles.

* * * * *